(12) United States Patent
Gumbrecht et al.

(10) Patent No.: US 8,088,576 B2
(45) Date of Patent: Jan. 3, 2012

(54) METHOD AND ASSEMBLY FOR DNA ISOLATION WITH DRY REAGENTS

(75) Inventors: Walter Gumbrecht, Herzogenaurach (DE); Peter Paulicka, Erlangen (DE); Manfred Stanzel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 896 days.

(21) Appl. No.: 11/587,581

(22) PCT Filed: Apr. 28, 2005

(86) PCT No.: PCT/EP2005/051941
§ 371 (c)(1),
(2), (4) Date: Oct. 25, 2006

(87) PCT Pub. No.: WO2005/106024
PCT Pub. Date: Nov. 10, 2005

(65) Prior Publication Data
US 2007/0219366 A1    Sep. 20, 2007

(30) Foreign Application Priority Data
Apr. 30, 2004 (DE) .......... 10 2004 021 780

(51) Int. Cl.
C12Q 1/68 (2006.01)
(52) U.S. Cl. ..................................... 435/6.1
(58) Field of Classification Search .................. None
See application file for complete search history.

(56) References Cited

U.S. PATENT DOCUMENTS

| | | | |
|---|---|---|---|
| 5,173,260 A * | 12/1992 | Zander et al. ................. 422/57 |
| 5,498,392 A | 3/1996 | Wilding et al. |
| 5,550,044 A | 8/1996 | Kosak et al. |
| 5,599,660 A | 2/1997 | Ramanujam et al. |
| 5,783,148 A * | 7/1998 | Cottingham et al. ........... 422/56 |
| 5,830,644 A | 11/1998 | West et al. |
| 5,882,903 A * | 3/1999 | Andrevski et al. .......... 435/91.2 |
| 5,955,351 A * | 9/1999 | Gerdes et al. .............. 435/287.2 |
| 5,972,386 A | 10/1999 | Burgoyne |
| 6,168,948 B1 * | 1/2001 | Anderson et al. .......... 435/287.2 |
| 6,221,581 B1 | 4/2001 | Engelhardt et al. |
| 6,361,958 B1 | 3/2002 | Shieh et al. |
| 6,403,339 B1 | 6/2002 | Bertling |
| 6,440,725 B1 * | 8/2002 | Pourahmadi et al. ...... 435/288.5 |
| 6,544,734 B1 * | 4/2003 | Briscoe et al. ................. 435/6 |
| 6,617,136 B2 | 9/2003 | Parthasarathy et al. |
| 2001/0012612 A1 | 8/2001 | Petersen et al. |
| 2002/0022261 A1 | 2/2002 | Anderson et al. |
| 2002/0045246 A1 | 4/2002 | McMillan et al. |
| 2002/0106686 A1 | 8/2002 | McKernan |
| 2003/0073110 A1 | 4/2003 | Aritomi et al. |
| 2004/0018611 A1 | 1/2004 | Ward et al. |
| 2004/0063197 A1 | 4/2004 | Tilles et al. |
| 2004/0063198 A1 | 4/2004 | Tilles et al. |
| 2004/0209354 A1 | 10/2004 | Mathies et al. |
| 2008/0241890 A1 | 10/2008 | Gumbrecht et al. |

FOREIGN PATENT DOCUMENTS

| DE | 102 36 460 A1 | 2/2004 |
|---|---|---|
| DE | 10236460 A1 | 2/2004 |
| EP | 0572057 | 12/1993 |
| WO | WO 95/06652 A | 3/1995 |
| WO | WO 9600301 A1 * | 1/1996 |
| WO | WO 99/33559 A | 7/1999 |
| WO | WO 99/33559 A | 8/1999 |
| WO | WO 02/072262 A | 9/2002 |
| WO | WO 2004/065010 A | 5/2004 |
| WO | WO 2004/065010 A | 8/2004 |

OTHER PUBLICATIONS

PCT/ISA/220.
McMillan W.A: "Real-time PCR with fully integrated specimen preparation", Phytopathology, St. Paul, US, Bd. 92, Nr. 6, Suppl, 27.7.02, S. S110, Date: Jul. 27, 2002.
Raja Siva et al: "Technology for automated, rapid, and quantitative PCR of reverse transcription-PCR clinical testing", Clinical Chemistry, May 2005, Bd. 51, Nr. 5, 03.03.05, S.882-890.
Dale, S.J., "Direct Microtiter Plate Sequencing of PCR-Amplified M13 Clones from Plaques Using Dried Reagents", Biotechniques, Feb. 1992, vol. 12, No. 2, pp. 194, 196-197.
Kaijalainen, S., et al., "An alternative hot start technique for PCR in small volumes using beads of wax-embedded reaction components dried in trehalose", Nucleic Acids Research, vol. 21, No. 12, pp. 2959-2960 (1993). Blair, P., et al., "Wax-embedded PCR Reagents", Cold Spring Harbor Laboratory Press, US, vol. 4, No. 3, pp. 191-194 (Dec. 1, 1994).
Office Action mailed on Feb. 27, 2009 for U.S. Appl. No. 11/587,567.
Office Action mailed on Nov. 5, 2009 for U.S. Appl. No. 11/587,567.

* cited by examiner

*Primary Examiner* — Christopher M. Babic
(74) *Attorney, Agent, or Firm* — Harness, Dickey & Pierce, P.L.C.

(57) ABSTRACT

A DNA isolation method by removal of constituents, interfering with a subsequent PCR is disclosed. According to an embodiment of the method, all substances and method steps are fully integrated into a closed unit (cartridge) for single use, which allows entry of a DNA-containing sample and DNA-binding substrates are used for isolating the released DNA. In particular, when the method is applied to DNA isolation from whole blood by disruption of white blood cells, the reagents, required for carrying out the cell disruption and other reactions, are stored in a form which is stable at room temperature. For disrupting the white blood cells and for DNA isolation, a dry stored lysis reagent is dissolved in an aqueous solution and brought into contact with the white blood cells. The corresponding assembly includes a unit, for housing DNA-containing biological containers and/or reagents, whereby at least one microchannel is provided to contain reagents, whereby the reagent is present in the microchannel as a dry mixture with a negligible vapor pressure, which forms a stable substance at room temperature.

14 Claims, 3 Drawing Sheets

METHOD AND ASSEMBLY FOR DNA ISOLATION WITH DRY REAGENTS

PRIORITY STATEMENT

This application is the national phase under 35 U.S.C. §371 of PCT International Application No. PCT/EP2005/051941 which has an International filing date of Apr. 28, 2005, which designated the United States of America and which claims priority on German Patent Application number 10 2004 021 780.7 filed Apr. 30, 2004, the entire contents of which are hereby incorporated herein by reference.

FIELD

The invention generally relates to a method for DNA isolation with dry reagents. The invention also generally relates to an associated assembly for carrying out the method.

BACKGROUND

For nucleic acid analysis to answer human genomic questions, e.g. in white blood cells from whole blood, the cells must firstly be broken up in a sample preparation step and the DNAs thereby released must subsequently be isolated. It is in this case necessary to remove blood constituents such as hemoglobin, immunoglobulins and lactoferrin, which could inhibit a subsequent PCR.

In the laboratory, these working steps are carried out according to a sufficiently well-known prior art. Besides other methods, for example, cells can be broken up (so-called lysis) with an alkaline solution (NaOH) and the DNAs can subsequently be bound to silica-coated magnet beads. By applying a magnetic field, the magnet beads laden with DNA are fixed and washed. The DNA isolated in this way can subsequently be used with or without beads for a PCR (Polymerase Chain Reaction).

In the prior art, the DNA-binding magnet beads are used as a suspension in a cell lysis buffer. All the working steps are carried out for example in 1.5 ml reaction vessels (so-called "Eppendorf" vessels). For example, 10 μl of whole blood is added to a predetermined volume of the bead suspension (e.g. 200 μl). The blood cells are thereby disintegrated and the DNAs are released. The magnet beads bind the DNA and form a DNA/bead complex. Such a DNA/bead complex can subsequently be fixed by a magnetic field on the vessel wall of the Eppendorf tuber, so that washing steps can be carried out to remove PCR-inhibiting substances. The PCR can subsequently be carried out.

Conduct of the latter method is contingent on the provision of laboratory equipment such as the "Eppendorf" vessels (tubes), tube holding devices including magnets, pipetting equipment, cooling containers for reagents, and must be carried out by trained personnel while complying with safety rules (infection risk, waste disposal, etc.). A plurality of volumetric and highly accurate dosings of substances which are sometimes hazardous to health (e.g. NaOH) first be carried out by pipetting. These working steps are also time-consuming.

US 2002/0022261 A1 has already disclosed systems for miniaturized genetic analysis and associated operating methods, in which a cartridge with at least one input and a porous passage, which is intended to have DNA-binding properties, is used. Disintegration of cells takes place, to which end reagents are provided optionally on the vessel wall. Structured regions of the wall may furthermore be coated with DNA-binding materials, optionally also magnet beads. Overall a series of different proposals are provided there in order to perform the measurement for the genetic analysis, although a continuous method is still not carried out. A mixture for the isolation of DNA is furthermore known from EP 0 723 549 B1, this mixture especially containing silica gel, glass particles and at least one chaotropic salt.

Furthermore, WO 99/33559 A describes a device for separating and analyte from a fluid sample, which comprises the cartridge with a lysation chamber in the sample flow path, the cells of the sample being filtered out via a filter and disintegrated. The analyte separated in this way is fed to individual sensor chambers in the device for analysis.

SUMMARY

In at least one embodiment of the invention, the PCR is performed entirely in an integrated miniaturized cartridge and in at least one embodiment, an associated assembly is provided.

In the scope of at least one embodiment of the invention, a method includes disintegration of biological structures containing DNA, for example cells, bacteria or viruses. It is therefore possible to study whole blood samples in respect of DNA information in a particularly advantageous Besides the above prior art, at least one embodiment of the invention is also based on WO 02/0072262 A1 entitled "Analysis Device". This has already described the use of dryly stored, room-temperature stable reagents in microchannels or microcavities of a "chip card", which are put into solution by supplying water shortly before use. This prior art entails providing the dry reagents in a pre-portioned form, so that a quantitative analysis medium is obtained after dissolving. At least one embodiment of the present invention on the other hand, involves cell disintegration of a biological structure, for example the isolation of DNA from a whole blood sample for the purpose of subsequent PCR and/or analysis, the DNAs isolated from the sample being prepared-in a suitable way.

At least one of the following advantages, compared with the previously used laboratory method, are obtained with the method according to at least one embodiment of the invention:

- all the materials and methods are fully integrated in a closed single-use cartridge;
- it ensures that the reagents are held in a secure form not hazardous to health, which is stable when stored at room temperature;
- no manual working steps are necessary, other than injection of the blood sample;
- no direct contact takes place with materials that are hazardous to health, i.e. blood and reagent waste remain in the cartridge; the cartridge is small inexpensive to make in mass production.

The assembly according to at least one embodiment of the invention includes at least one of the following features:
  at least one microchannel or microcavity is provided. In the microchannel or the microcavity, the lysis medium is applied
  in particular with the inclusion of the film-forming agent with the substrate for the DNA on the wall of the channel.

A lysis medium introduced into the microchannel or microcavity has the following properties:
  lysis properties for white blood cells and/or other cells, bacteria, viruses;
  solid, or liquid with a negligible vapor pressure;
  stable at room temperature;

good adhesion to microchannel or microcavity walls.

In at least one embodiment, in a continuous method sequence, the DNA contained in the sample is released, collected as isolated DNA and suitably brought to the site of the PCR or a detection.

BRIEF DESCRIPTION OF THE DRAWINGS

Further details and advantages of the invention will be found in the following figure description of example embodiments with the aid of the drawings in conjunction with the patent claims.

DETAILED DESCRIPTION OF THE EXAMPLE EMBODIMENTS

Samples containing DNA will be defined in the following description. Such samples may be solutions of DNA in a liquid, but also DNA-containing suspensions of biological structures. Cells, bacteria or viruses, for example, are to be understood as biological structures in the present context. Disintegration of the biological structure is then necessary in order to release the DNA. If whole blood samples are used according to a human genomic task, for example, then cell disintegration of white blood cells in which the DNA is localized is necessary.

Figure 1:
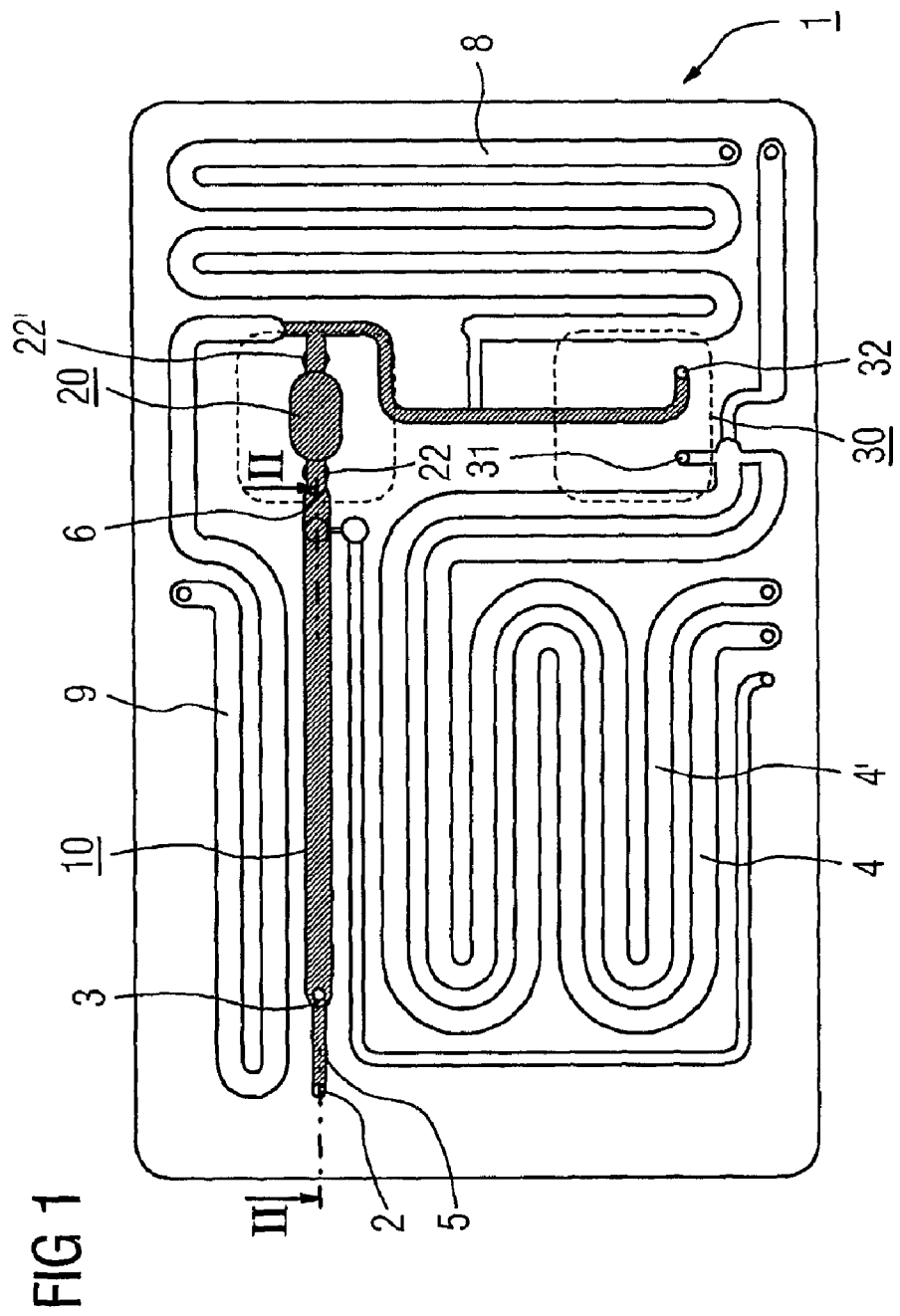
FIG. 1 shows the plan view of an analysis device (cartridge)

FIG. 1 represents an analysis device, which also as "cartridge" below and may be designed as a central or decentral measuring device. In particular, the analysis device is designed in the manner of a chip card ("lab-on-a-chip"), which contains all the aspects for treating and evaluating measurement samples. An associated control/readout device necessary for proper operation of the device is not shown in this context.

In detail the device includes a card-like body 1 made of plastic, which includes inlets and outlets for fluids. In particular, an inlet ("port") 2 is provided for introducing water and an inlet 3 ("port") is provided for introducing a measurement sample, for example blood. What is essential is that measurement samples and solvents are transported and combined via suitable fluidic devices 2 to 10, and in particular channels and cavities of different geometry.

Besides the aforementioned water and sample ports 2, 3, the fluidic devices specifically contain two reagent channels 4, 4' as well as a flow channel 5 with an outlet 6, a reception channel 8 for waste and a further fluidic channel 9. A central mixing region in the flow channel 5 for the sample preparation is denoted by 10.

After treatment of the sample in the mixing section 10 and after isolation of the DNA contained in the measurement sample, the released DNAs are collected and fed to a PCR chamber 20 for carrying out a PCR (Polymerase Chain Reaction).

A process for carrying out PCR especially with dry reagents in an assembly according to FIG. 1 is described in detail in the parallel patent application in the name of the Applicant with the same application priority entitled "PCR process and arrangement for DNA amplification using dry reagents".

Besides the PCR means, the card 1 ("cartridge") furthermore contains a detection module 30 with a feed 32 and discharge 31, as well as associated connections for sensor signal readout. Means for receiving reagents for the detection, for example channels 4 and 4', as well as for receiving waste such as blood and consumed reagent solutions, for example channels 8 and 9, are furthermore provided. This ensures an integration in which no substances hazardous to health can escape.

It can be seen from FIGS. 2 to 6 that the plastic card 1 of FIG. 1 with a water port 2 and a blood port 3 contains a flow channel 5 via which water as a washing liquid, and for example a blood or DNA solution or a cell/bacteria/virus suspension as a measurement sample, are introduced into the otherwise closed system. The waste is transferred via an outlet 6 into the waste channel 8, or into a waste cavity. On the opposite side from the plastic card 1, the flow channel 5 is covered with an adhesive film 7. In the central region of the flow channel 5, a mixing section 10 is formed in which the measurement samples are prepared especially for DNA isolation from whole blood.

The DNA isolation from whole blood takes place via disintegration of the white blood cells. To this end, the cells are broken up chemically with a lysis reagent and the DNA contained in them is released and collected. In particular, the known procedure is employed in which the DNA is bound at least temporarily via so-called magnet beads after disintegration of the cell, and is concentrated by an external magnetic field.

Figure 2:
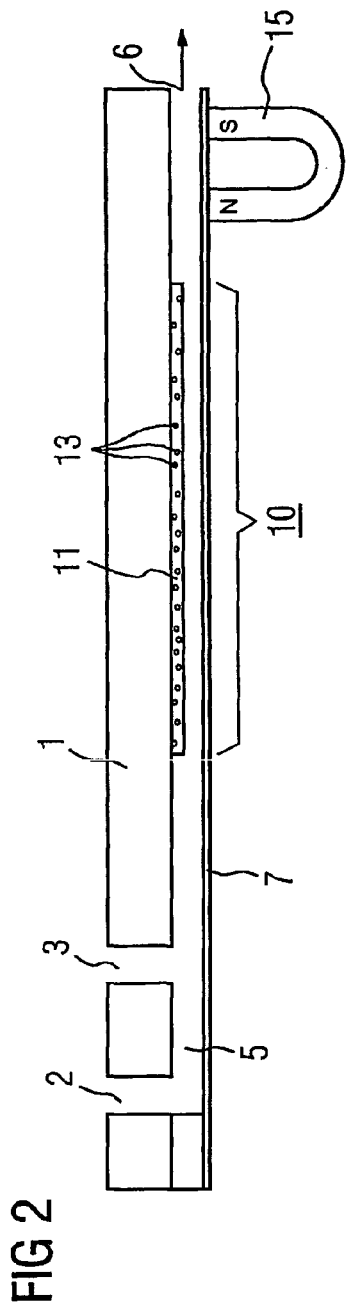
FIG. 2 to FIG. 6 respectively show a detail of FIG. 1 in longitudinal section along the line II-II to illustrate the DNA isolation from whole blood, the individual FIGS. 2 to 6 respectively containing different function steps.

It can be seen especially in FIG. 2 that a storage-stable dry substance 11, which is water-soluble, is arranged in a region 10 of the flow channel S in the plastic card 1. Storage stability in this context is intended to mean that the solid can be stored for several months at room temperature while preserving the property of inducing the sample disintegration.

Figure 3:
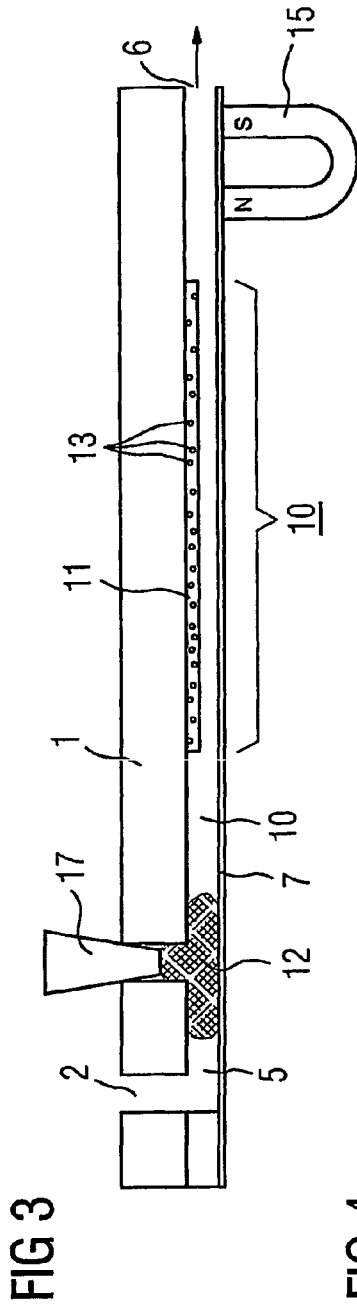

The dry substance 11 exhibits good adhesion to the walls of the flow channel in FIGS. 2 and 3. This may, for example, be achieved by adding a film-forming agent. To this end, specifically, a mixture 11 of a known lysis reagent with magnet beads 13 is arranged over a large area in the region of the mixing section 10. A magnet 15 is furthermore symbolically indicated, which illustrates the magnetic treatment to concentrate the magnet beads 13 with DNA bound on them.

Figure 4:
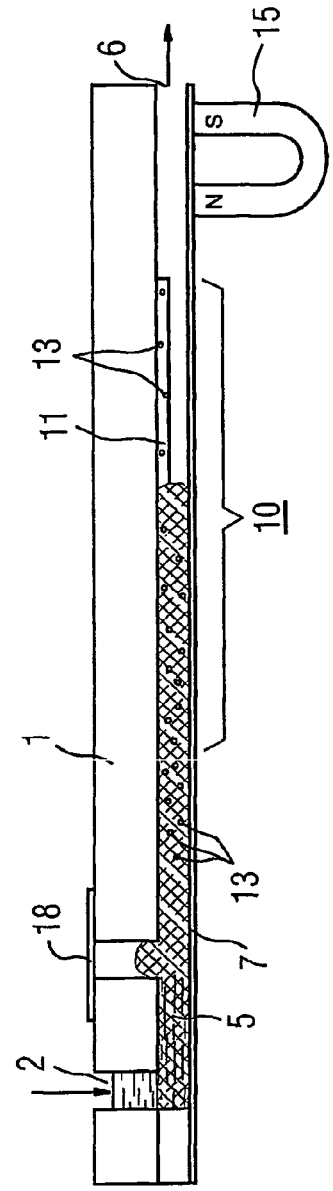

It can be seen from FIG. 3 and FIG. 4 that whole blood 12 is introduced into the measurement system via a pipette tip 17 in the arrangement according to FIG. 2. The port 3 is closed by way of an adhesive film 18 after the sample has been introduced.

Water or a buffer solution is introduced via the port 2. Water or buffer solution mixes with the blood sample 12 along the mixing section, the lysis reagent 11 together with the magnet beads 13 likewise being dissolved or suspended, and activated. Accordingly, the cell walls of the white blood cells are broken up by the lysis reagent and the DNAs thereby released are bound to the surface of the magnet beads.

According to FIG. 4, the water/the buffer solution thus dilutes the blood sample and simultaneously dissolves the lysis reagent, which serves to ensure disintegration of the white blood cells. Likewise, moreover, the magnet beads of the mixture 11 which lie on the wall of the channel are brought into solution or suspended, the DNAs being bound via these magnet beads 13. In this way, the following essential method steps, specifically:

sample dilution,
    reagent dissolving/magnet bead suspension,
    cell disintegration and
    DNA binding are carried out in a single process.

Figure 5:
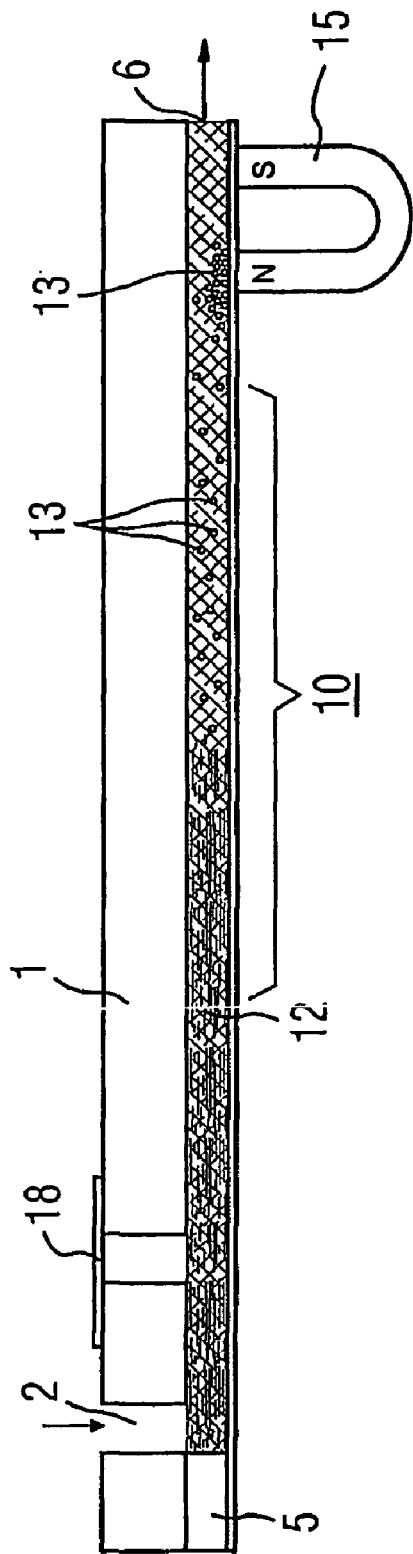
Figure 6:
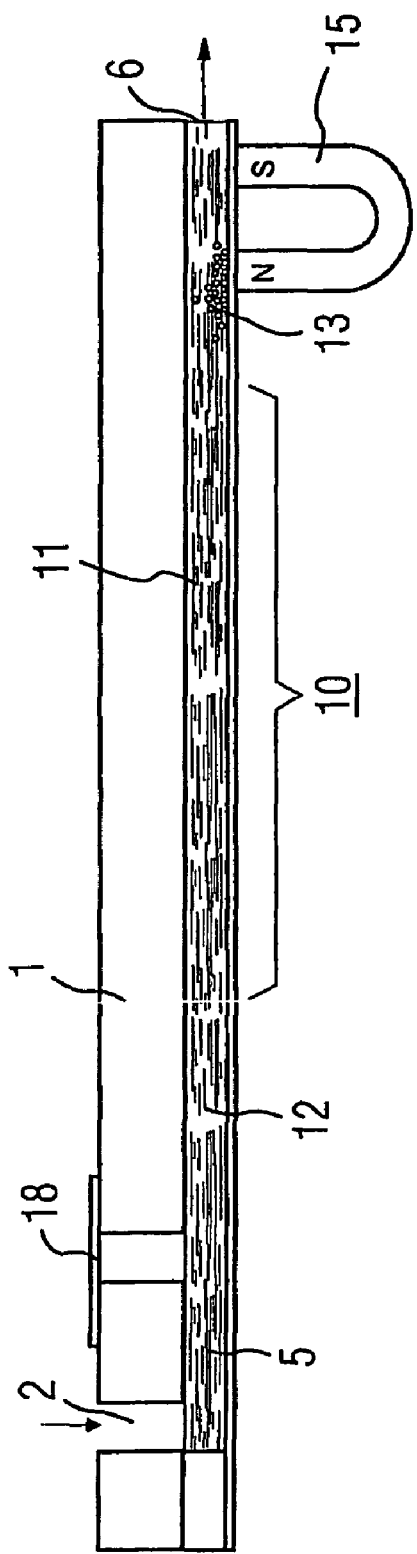

The latter is illustrated with the aid of FIG. 5. The DNA magnetically treatable via the magnet beads 13 can now be collected, while PCR-inhibiting substances are washed out by water or a buffer solution and discharged via the outlet 6.

As a result of the measures described above, according to FIG. 6 the DNA bound via the magnet beads 13 is concentrated on one of the magnet poles of the magnet 15. This DNA can be used for an analysis, a PCR in particular being carried out first.

As an alternative to employing mobile i.e. suspended magnet beads in combination with a magnetic field as a DNA-binder(s), it is also possible to use immobilized i.e. static DNA-binder(s), placed at the output of the cell disintegration channel. In this embodiment, the DNA released from the cells is extracted from the liquid stream when it leaves the cell disintegration channel by flowing over the static DNA-binder(s), and is bound on the DNA-binder(s). For example, hydrogels with DNA-binding capture molecules or the like may be envisaged as DNA-binder(s).

The method according to an embodiment of the invention and the associated assembly provide in particular one-stage, simple and rapid DNA isolation, which necessitates only a minimum of microfluidic devices, reagents and/or method steps.

The isolated DNA can subsequently be subjected to the PCR. PCR increases the concentration of the DNA to an analytically detectable value. The PCR can now be incorporated into the analysis process. The analysis then takes place in the detection module 30 according to FIG. 1, which will not be discussed in further detail here.

In summary, at least one embodiment of the invention implements the following measures:

the substrates introduced in the microchannel or microcavity have DNA-binding properties. To this end, for example, DNA-binding magnet beads may be used;

the lysis reagents and magnet beads are contained in particular together in a single dry matrix;

an input port is provided for a whole blood sample cell/bacteria/virus suspension);

at least one way for supplying water is provided. This may, for example, be a feed port for connection to an external water supply;

at least one way/device is optionally provided for admixing salts, for example in order to adjust a defined ionic strength;

at least one way/device (channels and cavities) is optionally provided for diluting the blood sample;

optionally further ways/devices, for example channels and cavities, are provided in order to prepare defined salt/buffer solutions for washing the bound DNA, e.g. DNA-magnet bead complex;

at least one way/device is provided, preferably outside the cartridge, so that blood or a blood/water, blood/buffer mixture can flow through the microchannel or microcavity coated with lysis/bead reagent;

at least one way/device is provided, for example at the output of the microchannel, for generating a magnetic field to fix the DNA/magnet bead complex in the PCR cavity, these ways/devices preferably lying outside the cartridge.

This ensures that the entire analysis process, including the sample preparation, takes place in the closed system constituted by a disposable cartridge made of environmentally friendly plastic.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for DNA isolation while removing constituents that interfere with a subsequent PCR, the method comprising:

integrating materials in a closed analysis single-use unit which allows a sample with DNA to enter;

releasing the DNA by using dry reagents stored in the unit in a form that is stable at room temperature;

isolating the released DNA using DNA-binding substrates, wherein the DNA-binding substrates are magnetic beads;

bringing a dry matrix, lying on a wall in a disintegration channel of the unit and including lysis reagents and the DNA-binding substrates, in contact with biological structures to disintegrate the biological structures containing the DNA, the magnetic beads being distributed in the dry matrix such that the DNAs released by contact with the lysis reagents are bound directly and simultaneously to the DNA-binding substrates; and collecting the substrates with the bound DNAs and transporting the collected substrates to a site of the PCR.

2. The method as claimed in claim 1, wherein white blood cells are used as the biological structures containing DNA.

3. The method as claimed in claim 2, wherein the lysis reagents are brought in contact with the white blood cells with the aid of water, the lysis reagents being stored dry and storage-stable.

4. The method as claimed in claim 1, further comprising diluting the sample with DNA, dissolving or suspending the dry reagents, disintegrating the biological structures and binding the DNA released by contact with the lysis reagents in a single step, after the sample with DNA is in the unit.

5. The method as claimed in claim 1, wherein the released DNA is bound and transported by the magnetic beads to at least one of a collection site and a reaction site.

6. The method as claimed in claim 1, wherein the magnetic beads are concentrated by applying a magnetic field.

7. The method as claimed in claim 6, wherein flowing magnetic beads are concentrated by a static magnetic field.

8. The method as claimed in claim 1, wherein the PCR is carried out by thermocycling with dryly-stored, water-soluble reagents at a reaction site.

9. The method as claimed in claim 1, wherein the sample with DNA is a blood sample put into the unit diluted and pumped through a reagent channel to a reaction channel for the PCR.

10. The method as claimed in claim 9, wherein residual blood, blood constituents and the reagent waste remain in the unit after the DNA isolation, so that a user cannot directly contact the residual blood, the blood constituents and the reagent waste.

11. The method as claimed in claim 1, wherein a disposable product is used as the single-use unit in which the PCR is performed.

12. The method as claimed in claim 11, wherein the disposable product is a cartridge.

13. The method as claimed in claim 12, wherein the cartridge is made of plastic.

14. The method as claimed in claim 1, wherein the dry matrix, having the magnetic beads therein, is adhered to the wall by adding a film-forming agent to the dry matrix.

* * * * *